(12) United States Patent
Snow et al.

(10) Patent No.: US 6,322,495 B1
(45) Date of Patent: Nov. 27, 2001

(54) METHOD FOR PLACING A FEEDING TUBE INSIDE A GASTRO-INTESTINAL TRACT

(75) Inventors: Todd H. Snow, Westborough; Michael P. Phalen, Marlborough, both of MA (US)

(73) Assignee: Scimed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/419,398

(22) Filed: Oct. 15, 1999

Related U.S. Application Data

(62) Division of application No. 09/007,500, filed on Jan. 15, 1998, now Pat. No. 5,989,231.

(51) Int. Cl.[7] .................. A61B 1/00; A61M 5/00
(52) U.S. Cl. .......... 600/114; 600/156; 600/115; 604/264; 604/500
(58) Field of Search .................. 600/114, 115, 600/120, 138, 139, 153, 156; 604/264, 280, 104, 117, 96; 606/191, 192, 198

(56) References Cited

U.S. PATENT DOCUMENTS

| D. 323,886 | 2/1992 | Picha et al. ............ D24/108 |
|---|---|---|
| D. 323,887 | 2/1992 | Picha et al. ............ D24/108 |
| 4,624,243 | 11/1986 | Lowrey et al. ............ 128/6 |
| 4,769,014 | 9/1988 | Russo ............ 604/270 |
| 5,007,900 | 4/1991 | Picha et al. ............ 604/106 |
| 5,112,310 | 5/1992 | Grobe ............ 604/175 |
| 5,152,277 | 10/1992 | Honda et al. ............ 128/4 |
| 5,188,596 | 2/1993 | Condon et al. ............ 604/101 |
| 5,279,553 | 1/1994 | Winkler et al. ............ 604/53 |
| 5,327,881 | 7/1994 | Greene ............ 128/11 |
| 5,356,391 | 10/1994 | Stewart ............ 604/175 |
| 5,518,406 | 5/1996 | Waters ............ 434/267 |
| 5,527,280 | 6/1996 | Goelz ............ 604/96 |
| 5,676,635 | 10/1997 | Levin ............ 600/120 |
| 5,733,241 | 3/1998 | King ............ 600/114 |
| 5,733,242 | 3/1998 | Rayburn et al. ............ 600/120 |
| 5,803,898 | 9/1998 | Bahour ............ 600/120 |
| 5,823,940 | 10/1998 | Newman ............ 600/116 |

OTHER PUBLICATIONS

Marks et al, "Access Routes for Enteral Nutrition", *The Gastroenterologist*, vol. 3, No. 2, Jun. 1995, pp. 130–139.

Chaurasia et al., "A Novel Technique for Percutaneous Endoscopic Gastrojejunostomy Tube Placement", *Gastrointestinal Endoscopy*, vol. 42, No. 2, 1995, pp. 165 to 168.

*Primary Examiner*—John P. Leubecker
(74) *Attorney, Agent, or Firm*—Testa, Hurwitz & Thibeault, LLP

(57) ABSTRACT

An optical feeding tube includes an elongated sheath having a first lumen for delivering nutrients to a gastrointestinal tract and an imaging device disposed in a second lumen. The imaging device provides visualization of an area adjacent a distal end of the elongated sheath. The imaging device can be an optical fiber extending from a proximal end to a distal end of the elongated sheath. The optical feeding tube can also include a retention device. The method for placing the feeding tube involves passing the feeding tube through an opening in the abdominal wall and into a gastro-intestinal tract while observing a passageway ahead of the feeding tube.

7 Claims, 6 Drawing Sheets

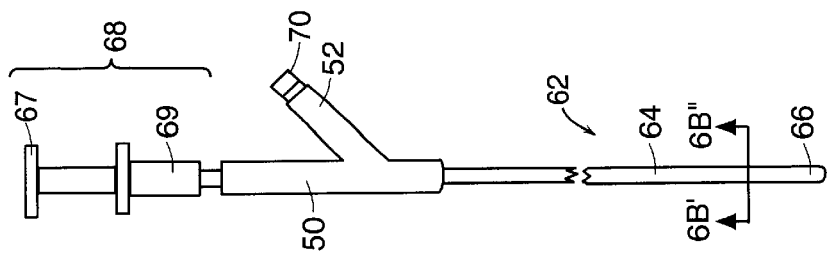
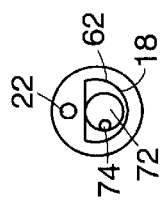
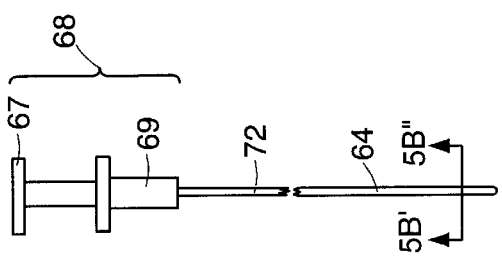
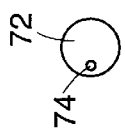
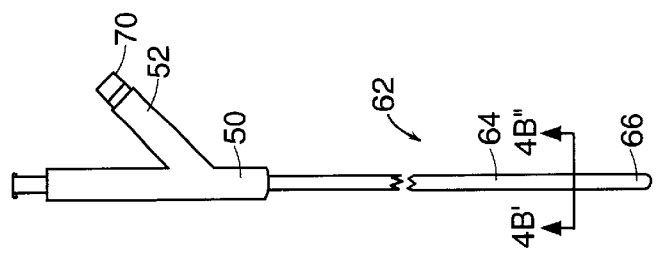
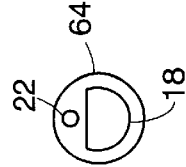

METHOD FOR PLACING A FEEDING TUBE INSIDE A GASTRO-INTESTINAL TRACT

RELATED APPLICATIONS

This application is a divisional of U.S. Ser. No. 09/007,500, filed Jan. 15, 1998, now U.S. Pat. No. 5,989,231, the disclosure of which is incorporated herein by reference in its entirety.

TECHNICAL FIELD

This invention relates to a feeding tube and, more particularly, to an improved feeding tube which allows visualization inside a gastrointestinal tract during the feeding tube placement or replacement.

BACKGROUND INFORMATION

Patients who are unable to take oral feedings can receive nutrients through a feeding tube by placing a distal end of the feeding tube in a patient's gastrointestinal tract and delivering nutrients to a proximal end of the feeding tube. Various procedural options exist for placing a feeding tube inside a patient.

One feeding tube placement method involves passing a nasoenteric feeding tube through a patient's mouth into his or her alimentary tract. This method, however, may not be suitable for certain patients, such as those with an obstruction in the alimentary tract at or beyond the pylorus, those with severe gastroesophageal reflux, those who require long-term enteral feeding in a non-hospital environment, and those who can support their caloric requirements with a self-administered enteral diet. Nasoenteric feeding tubes may also cause complications from either tube placement or enteral feeding. Complications resulting from a nasoenteric feeding tube placement include cribriform plate injuries, nasotracheal placement, alar cartilage erosion and tube occlusion which requires reinsertion of the tube. Complications resulting from enteral feeding include aspiration pneumonia, diarrhea, dehydration, and hyperglycemia.

Alternatively, a feeding tube may be placed surgically. In general, surgery involves providing an access to the stomach, inserting the feeding tube into the stomach, and securing the inserted feeding tube to the abdominal wall. Although surgical gastrostomy or jejunostomy allows accurate placement of the feeding tube, a surgical procedure is invasive, costly, and may be inappropriate for certain patients. In addition, surgery can cause complications such as bleeding, infection, pneumonia, myocardial injuries, and even death.

Still another way to place a feeding tube in a patient is to place it percutaneously or laparoscopically. Percutaneous and laparoscopic methods, however, are not widely utilized due to fear of blindly puncturing the abdomen. Percutaneous endoscopic gastrostomy overcomes this problem, but requires endoscopy which is uncomfortable for a patient. Several percutaneous endoscopic gastrostomy techniques exist including the pull technique, the push technique, and the introducer technique.

According to the pull technique, an endoscope is inserted into a patient's mouth and passed through the esophagus into the stomach. The patient's stomach is insufflated, and an opening to the stomach is made by inserting a needle into the stomach. An introducer catheter is introduced into the stomach through the opening. A guide wire is introduced into the stomach through the introducer, and an endoscopic snare tightens around the guide wire. The endoscope, the snare, and the guide wire are pulled out of the patient's mouth. A feeding tube is attached to an end of the guide wire extending from the mouth, and the guide wire extending from the stomach is pulled. This motion pulls the feeding tube through the esophagus and the stomach and positions the feeding tube such that the end of the feeding tube with the retention device remains inside the stomach, while the rest of the feeding tube remains outside the stomach.

The push technique is similar to the pull technique, except that the feeding tube is pushed through the abdominal wall over the guide wire, rather than being attached and pulled into the stomach. The guide wire is placed inside the patient in the same manner as in the pull method.

The introducer technique differs from the push and pull techniques in that the feeding tube is inserted through the abdominal wall and not through the mouth. After an endoscope is advanced into the stomach, a T-fastener is placed to move the stomach close to the abdominal wall. A needle is inserted through the abdominal wall into the stomach to create an opening. A guide wire is advanced through the opening, and an introducer with a peel-away sheath is passed over the guide wire. The introducer is then removed, and a gastrostomy tube is inserted into the stomach through the peel-away sheath. The feeding tube is a catheter with a Foley balloon at its distal end. The balloon is inflated to retain the feeding tube inside the stomach. The sheath is then peeled away, leaving behind the feeding tube.

Since proper feeding tube placement in a jejunum is more difficult than placing the feeding tube in a stomach, a jejunostomy tube is typically placed through a gastrostomy tube already positioned in a patient. A jejunostomy tube is typically longer and has a smaller cross section than a gastrostomy tube. Existing jejunostomy method, however, requires the use of an endoscope to provide visualization while feeding the tube through a duodenum into a jejunum. A guide wire is inserted through the gastrostomy tube and the jejunostomy tube is advanced over the guide wire into a jejunum under endoscopic guidance.

With existing feeding tube placement methods, feeding tube placement in a patient can be an unpleasant experience. However many patients must also go through feeding tube replacement. Approximately 70% of all patients receiving gastrostomy or jejunostomy feeding need long term feeding, which requires replacement of the feeding tube on a regular basis. During gastrostomy tube replacement, it is critical that the replacement tube is properly placed within the gastric cavity, and not into peritoneal space. Existing replacement method involves removing the tube in place and simply inserting the replacement tube into the gastric cavity through an existing opening. Physicians must endoscope the patient during this replacement procedure or send the patient to radiology to confirm proper tube replacement. Therefore, accurate feeding tube replacement can be invasive and burdensome to the patient. A feeding tube that is capable of accurate placement and replacement with minimal invasiveness to the patient would be useful.

SUMMARY OF THE INVENTION

The invention relates to an optical feeding tube. The optical feeding tube permits visualization of a passageway ahead of a distal end of the feeding tube, while the feeding tube is being placed in a patient, thereby eliminating the need for endoscopy. The optical feeding tube performs ideally as replacement feeding tubes. The optical feeding tube, however, may also be used for initial feeding tube placement when used according to the introducer method.

In general, in one aspect, the invention features an optical feeding tube which includes an elongated sheath having a first lumen for delivering nutrients to a gastro-intestinal tract and a second lumen. An imaging device is disposed in the second lumen. The imaging device provides visualization of an area adjacent a distal end of the elongated sheath.

Embodiments of this aspect of the invention include the following features. In some embodiments, the imaging device comprises an optical fiber extending from a proximal end to a distal end of the elongated sheath. In other embodiments, the optical feeding tube further includes a retention device disposed at a distal end of the elongated sheath. The retention device prevents movement of the feeding tube after placement. One example of the retention device is a balloon. In this embodiment, the elongated sheath includes a third lumen for transporting a fluid to and from the balloon. Another example of the retention device is a bolster.

In general, in another aspect, the invention features a method for placing a feeding tube inside a gastro-intestinal tract. According to the method, a distal end of the feeding tube is inserted into an opening which extends through an abdominal wall into a stomach cavity. The feeding tube includes an elongated sheath having a first lumen for delivering nutrients and a second lumen. An imaging device is disposed in the second lumen. The feeding tube is passed through the opening into the gastrointestinal tract under observation. A passageway ahead of a distal end of the feeding tube can be observed by looking into a proximal end of the imaging device. The distal end of the feeding tube is positioned at a desired location within the gastro-intestinal tract. In one example, the distal end of the feeding tube is placed in a stomach cavity. In another example, the distal end of the feeding tube is placed in a jejunum. In some embodiments, the method further includes the following additional steps. Initially, an opening which extends through the abdominal wall into the stomach cavity is made. A guide wire is advanced through the opening. An introducer with a sheath is passed over the guide wire. The feeding tube is inserted through the sheath.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 4A is a plan view of an optical feeding tube.

FIG. 4B is a cross section view of the optical feeding tube of FIG. 4A taken along line 4B'–4B".

FIG. 5A is a plan view of a stylet with a push pull deflectable handle.

FIG. 5B is a cross section view of the stylet of FIG. 5A taken along line 5B'–5B".

FIG. 6A is a plan view of the optical feeding tube of FIG. 4A having the stylet of FIG. 5A inserted through the feeding lumen.

FIG. 6B is a cross section view of the optical feeding tube of FIG. 6A taken along 6B'–6B".

DESCRIPTION

Figures 1A, 1B:
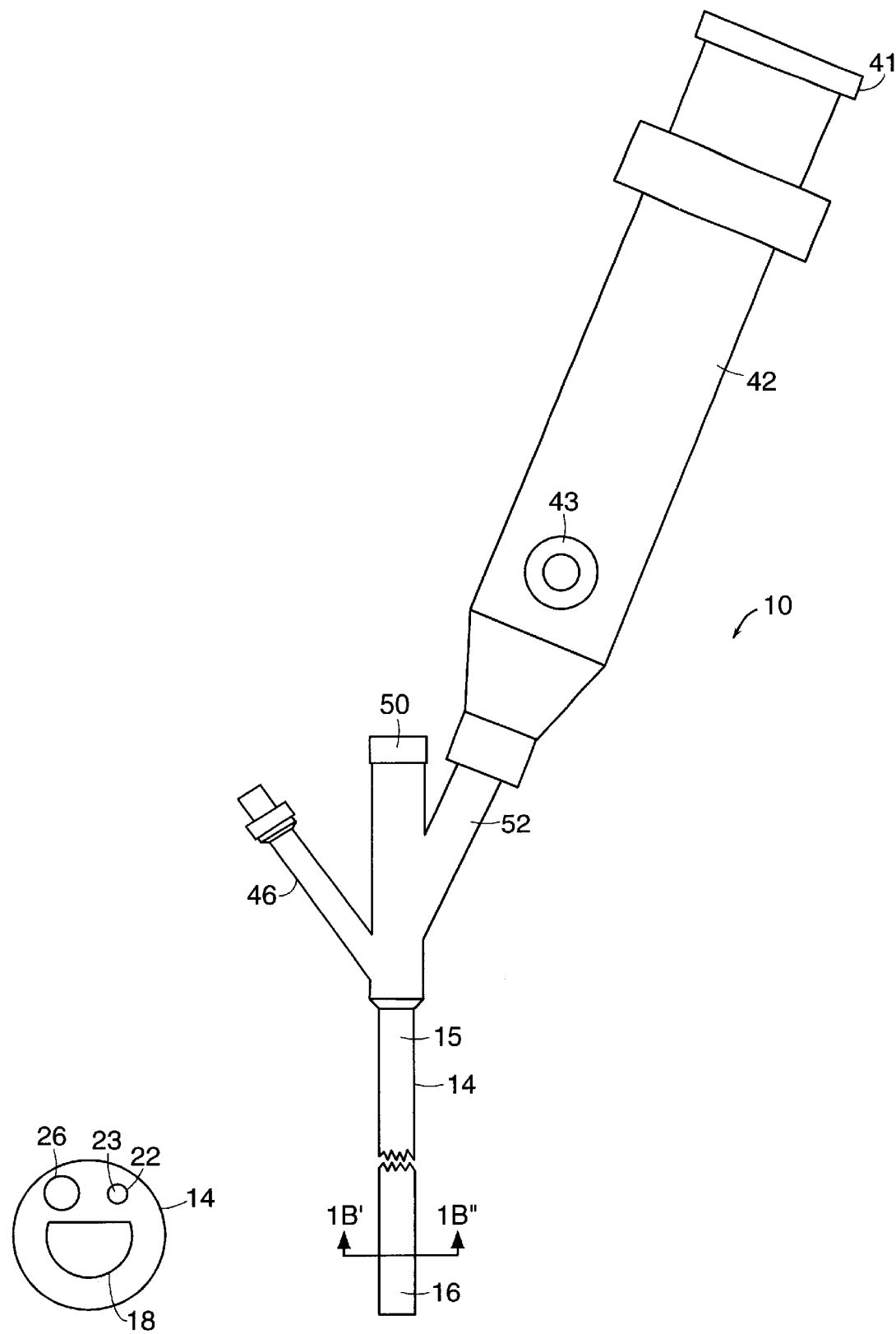
FIG. 1A is a plan view of an optical feeding tube having a balloon retention device.
FIG. 1B is a cross section view of the optical feeding tube of FIG. 1A taken along line 1B'–1B".

Referring to FIGS. 1A and 1B, an optical feeding tube 10 includes an elongated sheath 14 having several lumens 18, 22, 26 and ports 50, 52, 46 corresponding to each lumen 18, 22, 26 respectively. The lumens 18, 22, 26 extend from a distal end 16 of the elongated sheath 14 to a proximal end 15 of the elongated sheath 14, and each lumen 18, 22, 26 meets with its corresponding port 50, 52, 46 at the proximal end 15 of the elongated sheath 14. The elongated sheath 14 is constructed from a standard catheter material which renders it flexible enough to be inserted through a gastrointestinal tract. The elongated sheath 14, for example, may be constructed from silicone, a family of urethanes including polyurethane, Tecoflex® manufactured by Thermedics (Woburn, Mass.), Percuflex™ manufactured by Boston Scientific Corporation (Natick, Mass.), and Flexima™ mmanufactured by Boston Scientific Corporation (Natick, Mass.). The elongated sheath 14 and the ports 50, 52, 46 may be constructed as a single piece by a single material. The first lumen is a feeding lumen 18, which has a larger cross section area than the other lumens 22, 26. The feeding lumen receives nutrients at the feeding port 50 and delivers the nutrients to a gastro-intestinal tract of a patient.

The second lumen is an imaging lumen 22 which houses an imaging device 23. The imaging device 23 provides visualization of a passageway ahead of the feeding tube 10 while the feeding tube 10 is being placed in a gastro-intestinal tract of a patient. More specifically, the imaging device 23 provides visualization of an area adjacent the distal end 16 of the elongated sheath 14. The imaging device 23, for example, may comprise a bundle of optical fibers, extending from the proximal end 15 to the distal end 16 of the elongated sheath 14 and a lens in communication with the optical fibers disposed at the distal end 16. The optical fibers, for example, may be coextruded in the second lumen. The imaging device port 52 includes a coupler (not shown) to which a handle 42 connects. The handle 42 includes an eye piece 41 and a light source connector 43 to which an external light source (not shown) connects. The external light source provide visualization by transmitting light through the imaging device and illuminating an area near the distal end 16 of the elongated sheath 14. A person placing the feeding tube 10 can look into the eye piece 41 and observe the illuminated gastro-intestinal tract of a patient, while placing the feeding tube 10 inside the stomach cavity or the jejunum of the patient.

The optical feeding tube 10 further includes a retention device (not shown) disposed at the distal end 16 of the elongated sheath 14. In the embodiment of FIGS. 1A and 1B, the retention device is a balloon. The elongated sheath 14 includes a third lumen or a fluid lumen 26 through which fluid travels to and from the balloon to inflate and deflate the balloon. The balloon functions as a retention device when inflated. During the feeding tube 10 placement, the balloon remains deflated to facilitate insertion of the feeding tube 10 through the abdominal wall. Once the feeding tube 10 is properly positioned inside a gastro-intestinal tract, the balloon is inflated to prevent movement of the feeding tube 10. More specifically the balloon prevents the feeding tube 10 from sliding out of the stomach. A fluid port 46 in communication with the fluid lumen 26 at the distal end 15 of the elongated sheath 14 receives fluid from an external fluid source (not shown).

Figures 2A, 2B:
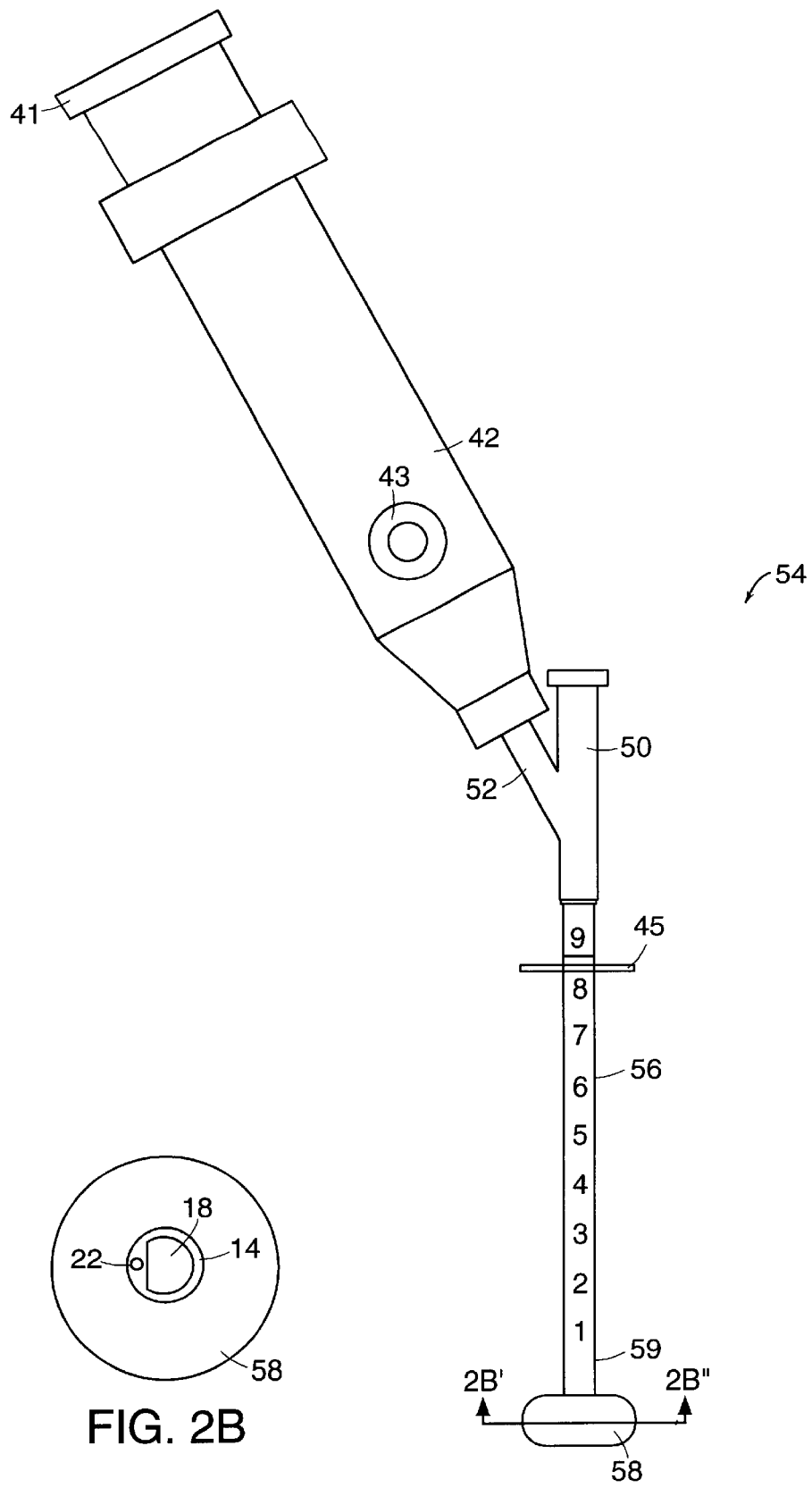
FIG. 2A is a plan view of an optical feeding tube having a bolster retention device.
FIG. 2B is a cross section view of the optical feeding tube of FIG. 2A taken along line 2B'–2B".

Referring to FIGS. 2A and 2B, an optical feeding tube 54 includes an elongated sheath 56 having a feeding lumen 18 and an imaging lumen 22. A feeding port 50 communicates with a proximal end of the feeding lumen 18. An imaging device port 52 communicates with a proximal end of the imaging lumen 22. A coupler (not shown) connects a handle 42 with the imaging device port 52. The handle 42 includes an eye piece 41 and a light source connector 43. The elongated sheath 56 has numbers from 1 to 9 displayed on its outer surface. These number assist in monitoring the feeding tube 54 movement, while the feeding tube 54 is placed inside a patient.

The elongated sheath 54 further includes a bolster 58 which functions as an internal retention device. Several types of bolsters are available for use with a feeding tube. For example, the optical feeding tube 54 may include a deformable bolster, a hollow sleeve surrounding and restricting the bolster and a rip-cord (not shown). While the optical feeding tube 54 is being inserted through the abdominal wall, the sleeve surrounding the bolster 58 restrains its figure. Once the distal end 59 of the feeding tube 54 is positioned inside the gastro-intestinal tract, the rip-cord is pulled and the sleeve is ripped, thereby exposing the full figure of the bolster 58. The extended bolster 58 has a cross section area larger than a cross section area of the elongated sheath 56 and the opening through which the feeding tube 54 was inserted. The sleeve is removed and the bolster 58 keeps the feeding tube 54 from movement. Any bolster known to those skilled in this art may be used with the optical feeding tube 54. The optical feeding tube 54 further includes an external retention device 45. The external retention device 45 is slidably mounted on the body of the elongated sheath 56 prior to the feeding tube 54 placement. Once the optical feeding tube 54 is positioned, the external retention device 45 is placed agains the abdomen, to further prevent movement of the feeding tube 54.

Figure 3:
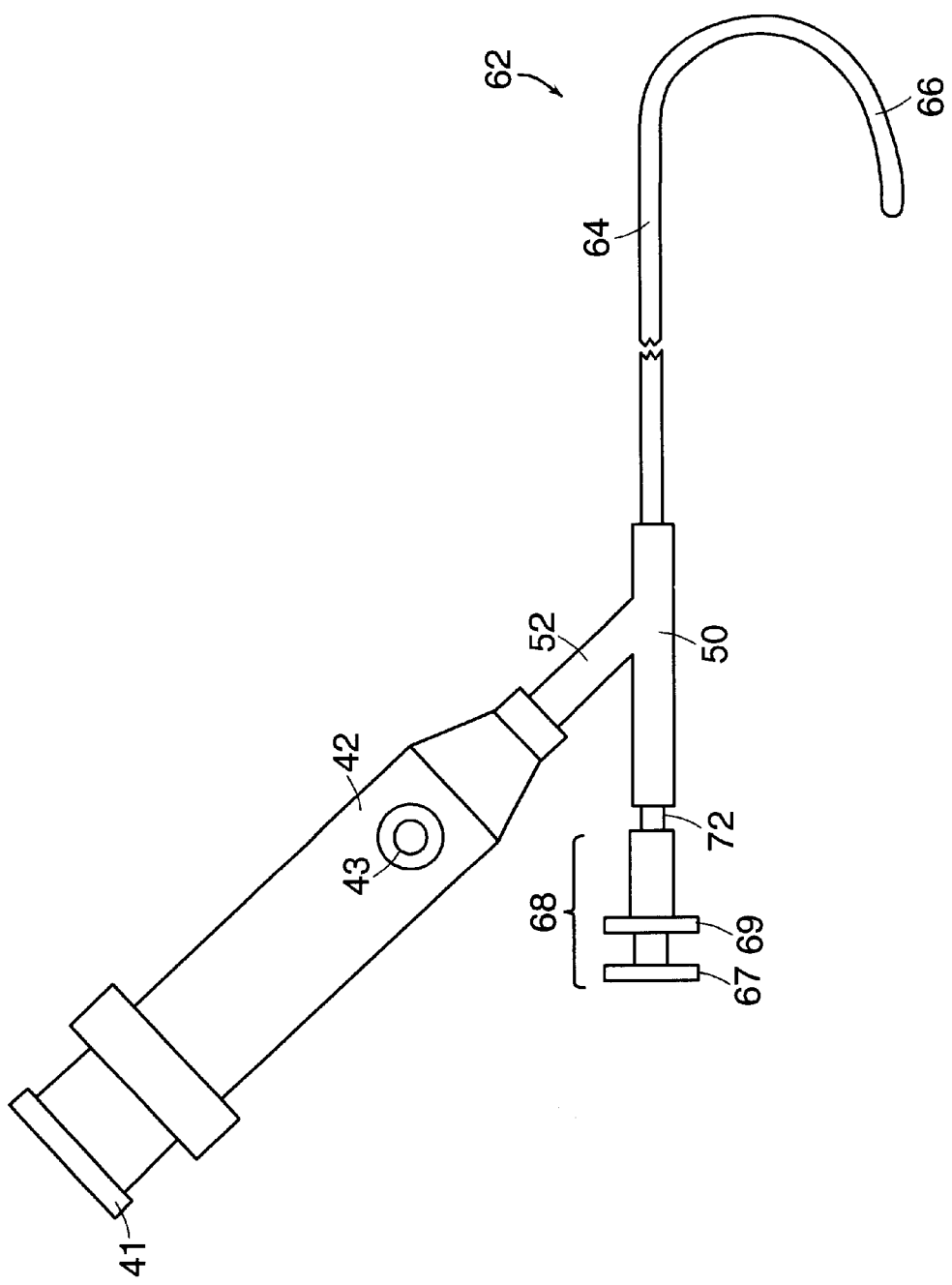
FIG. 3 is a plan view of a deflectable optical feeding tube.

Referring to FIG. 3, an optical feeding tube 62 is deflectable. A deflectable feeding tube facilitates its insertion through a gastro-intestinal tract. The optical feeding tube 62 includes an elongated sheath 64 having a deflectable tip 66. The tip 66 deflects by deflecting a stylet 72 inserted in a feeding lumen of the feeding tube 62. FIGS. 4A and 4B show an optical feeding tube 62 of FIG. 3. The optical feeding tube 62 includes an elongated sheath 64 having a feeding lumen 18 and an imaging lumen 22. An imaging device port 52 has a coupler (not shown) at the proximal end for connecting a handle 42 to the port 52. FIGS. 5A and 5B show a deflectable stylet 72 insertable in the feeding lumen 18 of the optical feeding tube 62 of FIG. 4A. The stylet 72 includes a deflecting wire 74 and a deflecting handle 68. The deflecting handle 68 operates in a push pull mode. The deflecting handle 68 includes a piston member 67 and a receptacle member 69. As the piston member 67 pushes against the receptacle member 69, the deflecting wire 74 deflects. Conversely, as the piston member 67 pulls away from the receptacle member 69, the deflecting wire 74 straightens. Details of a push-pull deflection mechanism is well known to those skilled in the relevant art and do not constitute an inventive aspect. As illustrated in FIGS. 6A and 6B, the stylet of FIG. 5A is inserted and secured into the feeding lumen 18 of the optical feeding tube 62 of FIG. 4A. The optical feeding tube 62 is then inserted into a patient's gastro-intestinal tract. During the insertion, the tip 66 may be deflected by adjusting relative positions between the piston member 67 and the receptacle member 69 of the deflecting handle 68. FIG. 6A shows the feeding tube 62 in a straight position and FIG. 3 shows the feeding tube 62 with the tip 66 deflected. Once the feeding tube 62 is positioned inside the gastro-intestinal tract, the stylet 72 is removed and the feeding tube 62 is ready to receive nutrients.

Figure 7:
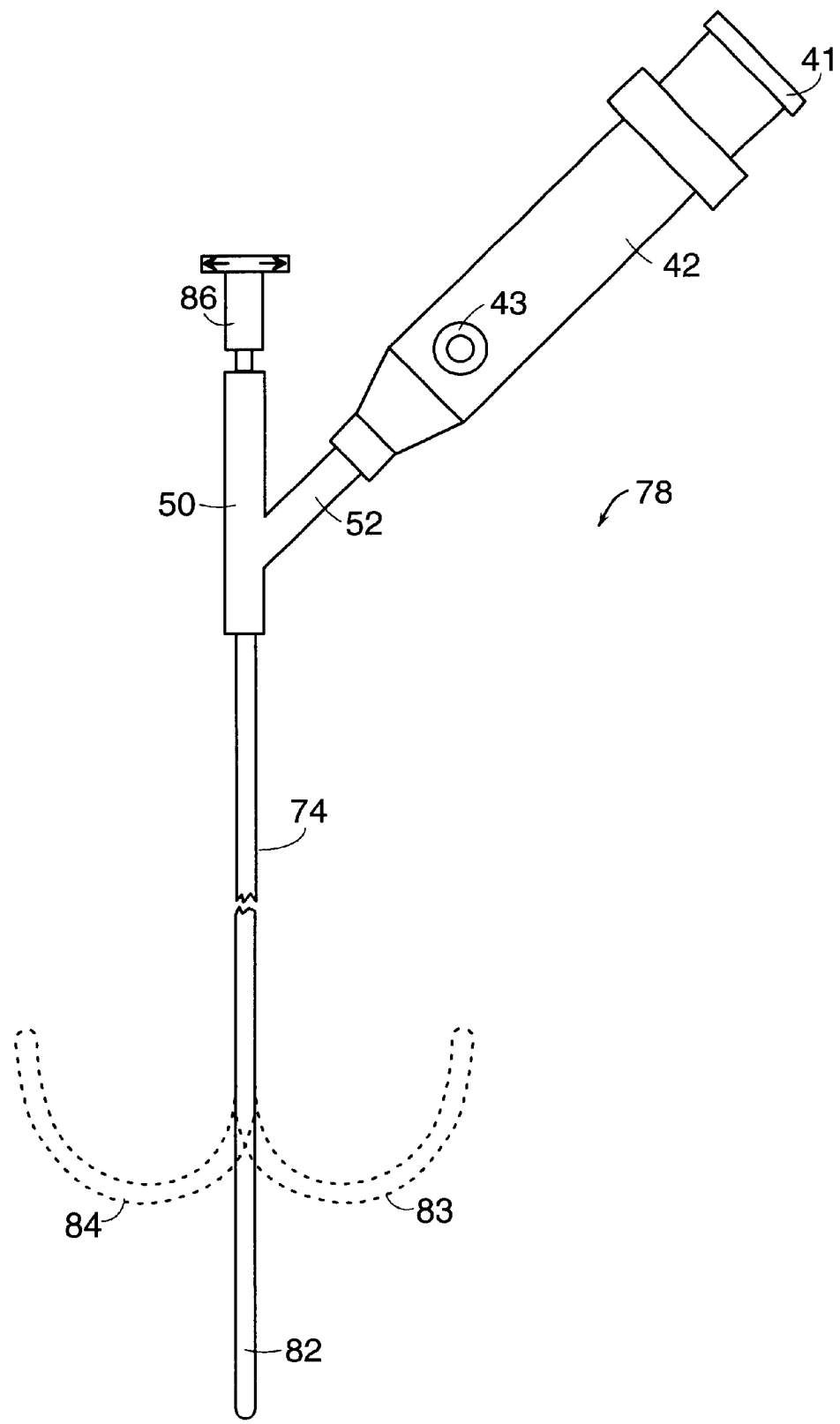
FIG. 7 is a plan view of another deflectable optical feeding tube.
Figure 10A:
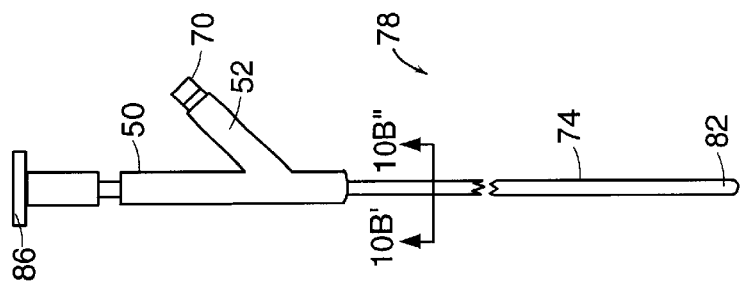
FIG. 10A is a plan view of the optical feeding tube of FIG. 8A having the stylet of FIG. 9A inserted through the feeding lumen.
Figure 10B:
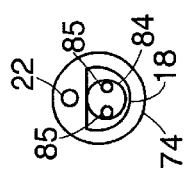
FIG. 10B is a cross section view of the optical feeding tube of FIG. 10A taken along line 10B'–10B".
Figure 9A:
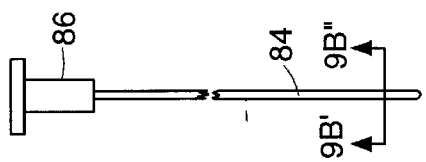
FIG. 9A is a plan view of a stylet deflectable in two directions.
Figure 9B:
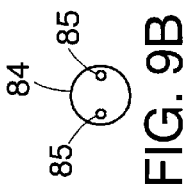
FIG. 9B is a cross section view of the stylet of FIG. 9A taken along line 9B'–9B".
Figure 8A:
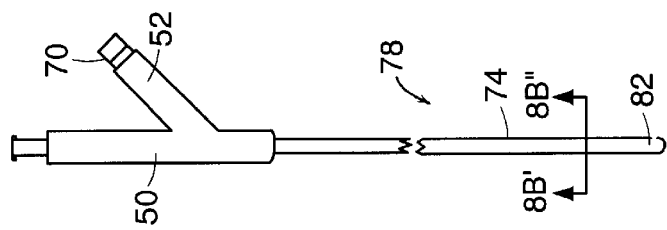
FIG. 8A is a plan view of an optical feeding tube.
Figure 8B:
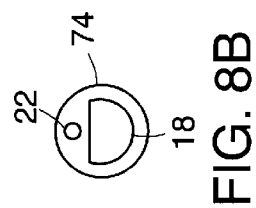
FIG. 8B is a cross section view of the optical feeding tube of FIG. 8A taken along line 8B'–8B".

Referring to FIG. 7, the optical feeding tube 78 includes an elongated sheath 74 and a deflectable tip 82. The tip 82 is deflectable in two directions as shown by phantom lines 83, 84. The tip 82 is deflected by deflecting a stylet inserted in a feeding lumen of the feeding tube 78. FIGS. 8A and 8B show the optical feeding tube 78 of FIG. 7 before a stylet is inserted into its feeding lumen 18. The optical feeding tube 78 is identical to the optical feeding tube 62 of FIGS. 4A and 4B. FIGS. 9A and 9B show a stylet 84. The stylet 84 includes two deflecting wires 85 and a deflecting handle 86. The stylet 84 deflects in one direction when the handle 86 rotates clockwise and in the opposite direction when the handle 86 rotates counter-clockwise. This type of steering mechanism is well known to those skilled in the art and does not constitute an inventive aspect. In operation, the stylet 84 is positioned inside the feeding lumen 18 of the optical feeding tube 78 prior to positioning the optical feeding tube 78 inside a gastro-intestinal tract of a patient. During the feeding tube placement, an operator controls deflection of the tip 82 by rotating the handle 86. Rotation of the handle 86 causes distal ends of the deflecting wires 85 to deflect, which in turn causes the deflectable tip 82 of the feeding tube 78 to deflect. Once the feeding tube 78 is properly positioned inside the gastro-intestinal tract, the stylet 84 is removed. The feeding tube 78 is then ready to receive nutrients.

The optical feeding tubes of the present invention may be used as both gastrostomy tubes and jejunostomy tubes. A difference between the two types of feeding tube is that a jejunostomy tube is typically longer and has a smaller cross-section area than a gastrostomy tube. A jejunostomy tube, for example, may have a cross-section diameter ranging from about 8 fr. to about 24 fr. A gastrostomy tube, for example, may have a cross-section diameter ranging from about 12 fr. to about 30 fr.

In one embodiment, an optical feeding tube of the present invention provides easy replacement of a gastrostomy tube, eliminating the need for an endoscopy or any other radiology procedures necessary to confirm proper tube placement. Once the existing feeding tube has been removed, a replacement feeding tube is simply inserted through an existing opening, which provides access to the stomach cavity through the abdominal wall. The operator inserts the replacement feeding tube under observation. The operator sees a passageway ahead of a distal end of the replacement feeding tube by looking into the eye piece. By visualizing the process, the operator can avoid placing the replacement feeding tube into a peritoneal space, which can injure the patient. Once the replacement feeding tube is properly placed inside the stomach cavity, an internal retention device is activated to hold the replacement feeding tube in place. An external retention device may also be placed against the abdomen to further prevent the replacement feeding tube movement.

In another embodiment, an optical feeding tube of the present invention is used as an initial gastrostomy tube. According to this embodiment, an opening which provides access to the stomach through the abdominal wall is first created. The opening, for example, may be created by inserting a needle through a patient's abdomen into his or her stomach cavity. A guidewire is advanced through the opening and an introducer with a peel-away sheath is passed over the guide wire. The introducer is then removed, and the optical feeding tube is inserted into the stomach through the sheath under observation. The sheath is then peeled away leaving behind the feeding tube. Unlike the existing introducer method, this method does not require an endoscope to confirm proper placement of the feeding tube.

In still another embodiment, the optical feeding tube is used as a jejunostomy tube. The jejunostomy tube, for example, is placed inside a gastro-intestinal tract through a regular gastrostomy tube already placed inside a patient. A regular gastrostomy tube does not have an imaging device. The jejunostomy tube is inserted into the feeding lumen of the regular gastrostomy tube. The jejunostomy tube is then inserted through a duodenum into a jejunum under visual guidance provided by the imaging device inside the jejunostomy tube. As a result, an endoscope is not required during the placement of the jejunostomy tube. The jejunostomy tube maybe inserted into a jejunum with an assistance of a guide wire. Alternatively, the jejunostomy tube having its own retention device may be placed inside a gastro-intestinal tract without the assistance of the gastrostromy tube.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A method for placing a feeding tube inside a gastro-intestinal tract, comprising:
   (a) inserting a distal end of the feeding tube into an opening which extends through an abdominal wall into a stomach cavity, the feeding tube comprising an elongated sheath having a first lumen for delivering nutrients and a second lumen, and an imaging device disposed in the second lumen;
   (b) passing the feeding tube through the opening into a gastro-intestinal tract while observing a passageway ahead of the feeding tube by looking into a proximal end of the imaging device; and
   (c) positioning the distal end of the feeding tube at a desired location within the gastro-intestinal tract.

2. The method of claim 1 further comprising activating a retention device to retain the feeding tube at the desired location.

3. The method of claim 2 wherein activating the retention device comprises inflating a balloon disposed at the distal end of the elongated sheath.

4. The method of claim 1 wherein step (c) comprises positioning the distal end of the feeding tube in the stomach cavity.

5. The method of claim 1 wherein step (c) comprises positioning the distal end of the feeding tube in a jejunum.

6. The method of claim 1 wherein step (b) comprises deflecting the distal end of the feeding tube to accommodate a curvature of the gastrointestinal tract.

7. The method of claim 1 further comprising:
   making an opening through the abdominal wall into the stomach cavity;
   advancing a guide wire through the opening;
   passing an introducer with a sheath over the guide wire;
   and wherein step (a) comprises inserting the feeding tube through the sheath.

* * * * *